(12) United States Patent
Christen

(10) Patent No.: US 9,681,902 B2
(45) Date of Patent: Jun. 20, 2017

(54) ATTACHMENT DEVICE FOR A BONE PLATE

(75) Inventor: Alexis Christen, Bern (CH)

(73) Assignee: Stryker European Holdings I, LLC, Kalamazoo, MI (US)

(*) Notice: Subject to any disclaimer, the term of this patent is extended or adjusted under 35 U.S.C. 154(b) by 147 days.

(21) Appl. No.: 13/371,916

(22) Filed: Feb. 13, 2012

(65) Prior Publication Data

US 2013/0211461 A1    Aug. 15, 2013

(51) Int. Cl.
*A61B 17/80* (2006.01)

(52) U.S. Cl.
CPC .......... *A61B 17/80* (2013.01); *A61B 17/8061* (2013.01); *A61B 17/8057* (2013.01)

(58) Field of Classification Search
CPC ........................ A61B 17/8061; A61B 17/746
USPC .... 606/279, 280, 70, 71, 281, 286, 288, 289
See application file for complete search history.

(56) References Cited

U.S. PATENT DOCUMENTS

| | | | |
|---|---|---|---|
| 3,824,995 A | 7/1974 | Getscher et al. | |
| 3,842,825 A | 10/1974 | Wagner | |
| 4,120,298 A | 10/1978 | Fixel | |
| 4,263,904 A | 4/1981 | Judet | |
| 4,506,662 A | 3/1985 | Anapliotis | |
| 4,565,193 A | 1/1986 | Streli | |
| 4,973,332 A * | 11/1990 | Kummer | A61B 17/746 606/304 |
| 5,015,248 A | 5/1991 | Burstein et al. | |
| 5,275,601 A | 1/1994 | Gogolewski et al. | |
| 5,462,547 A | 10/1995 | Weigum | |
| 5,591,168 A | 1/1997 | Judet et al. | |
| 5,709,686 A | 1/1998 | Talos et al. | |
| 5,973,223 A | 10/1999 | Tellman et al. | |
| 6,221,073 B1 * | 4/2001 | Weiss et al. | 606/60 |
| 6,338,734 B1 | 1/2002 | Burke et al. | |
| 6,503,281 B1 | 1/2003 | Mallory | |
| 6,652,530 B2 | 11/2003 | Ip et al. | |
| 7,229,444 B2 | 6/2007 | Boyd | |

(Continued)

FOREIGN PATENT DOCUMENTS

| | | |
|---|---|---|
| EP | 0007393 A1 | 2/1980 |
| EP | 0615728 A2 | 9/1994 |

(Continued)

OTHER PUBLICATIONS

European Search Report for Application No. EP12000914 dated Jun. 4, 2012.

*Primary Examiner* — Samuel Hanna
(74) *Attorney, Agent, or Firm* — Lerner, David, Littenberg, Krumholz & Mentlik, LLP

(57) ABSTRACT

An attachment device for attaching a bone plate to a bone having a medullary canal is provided. The attachment device comprises a central portion having a recess to accommodate the bone plate and at least two lateral fixation support members projecting from the central portion. The lateral fixation support members are arranged on opposite sides of the central portion, wherein each lateral fixation support member comprises a hole extending through the lateral fixation support member and are adapted to accommodate a fixation element therethrough to fix the attachment device to bone. The angles of the hole axes of the holes are different with respect to a perpendicular bisector of the centers of the holes and the hole axes lie outside of the medullary canal.

10 Claims, 7 Drawing Sheets

(56) References Cited

U.S. PATENT DOCUMENTS

| | | | |
|---|---|---|---|
| 7,695,472 B2 | 4/2010 | Young | |
| 7,722,653 B2 | 5/2010 | Young et al. | |
| 7,740,648 B2 | 6/2010 | Young et al. | |
| 7,905,883 B2 | 3/2011 | Bruecker et al. | |
| 2004/0225291 A1 | 11/2004 | Schwammberger et al. | |
| 2004/0236337 A1 | 11/2004 | Deloge et al. | |
| 2005/0010226 A1* | 1/2005 | Grady et al. | 606/69 |
| 2005/0049595 A1 | 3/2005 | Suh et al. | |
| 2005/0101959 A1 | 5/2005 | Mitkovic | |
| 2005/0165400 A1* | 7/2005 | Fernandez | A61B 17/8057 606/281 |
| 2006/0217722 A1 | 9/2006 | Dutoit et al. | |
| 2006/0264946 A1* | 11/2006 | Young | A61B 17/1728 606/915 |
| 2009/0171399 A1 | 7/2009 | White et al. | |
| 2010/0145339 A1* | 6/2010 | Steffen | 606/71 |
| 2010/0262194 A1* | 10/2010 | Wagner | A61B 17/80 606/286 |

FOREIGN PATENT DOCUMENTS

| | | | |
|---|---|---|---|
| EP | 0934731 | A1 | 8/1999 |
| FR | 1599483 | A | 7/1970 |
| FR | 2530453 | A1 | 1/1984 |
| GB | 2331244 | A | 5/1999 |
| GR | 1003502 | B2 | 1/2001 |
| SU | 1634260 | A1 | 3/1991 |
| WO | 0154601 | A1 | 8/2001 |
| WO | 02096309 | A1 | 12/2002 |
| WO | 2006097729 | A1 | 9/2006 |
| WO | 2009064643 | A1 | 5/2009 |

\* cited by examiner

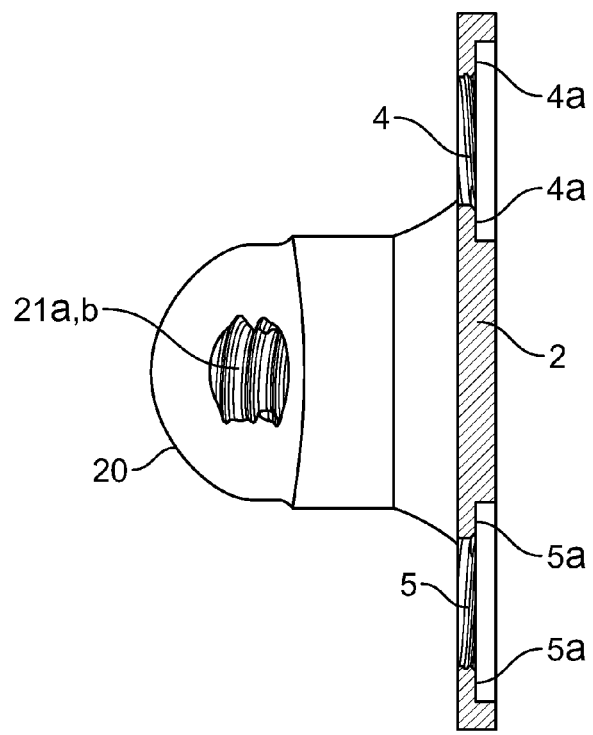
A-A   FIG. 3
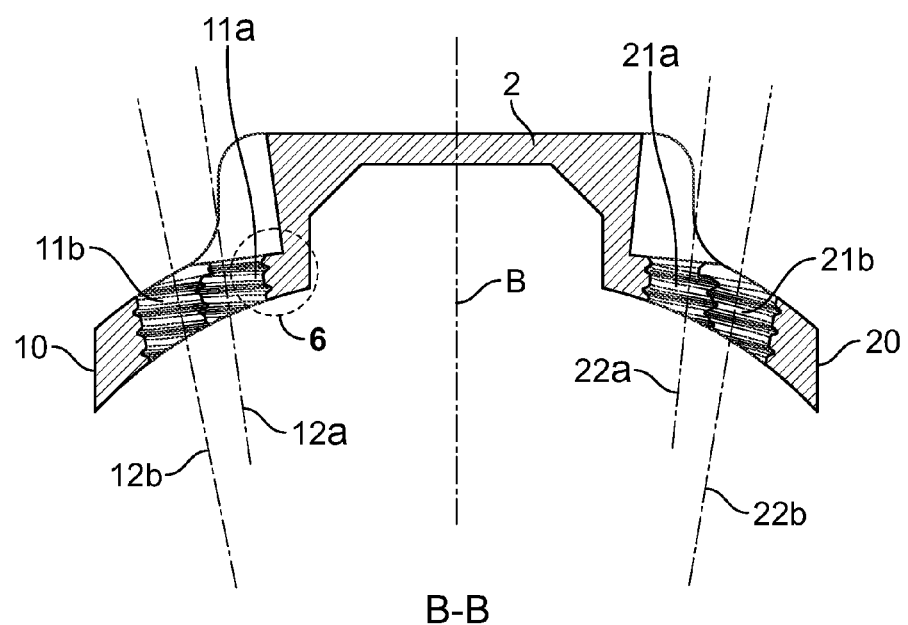
B-B
FIG. 4

ATTACHMENT DEVICE FOR A BONE PLATE

FIELD OF THE TECHNOLOGY

The present invention generally relates to bone plates, and in particular, to attachment devices for attaching bone plates to bone.

BACKGROUND OF THE INVENTION

Bone plates for fracture treatment are typically fixed to bone substantially parallel to a longitudinal bone axis using screws or other fixation elements. The bone plates have to be firmly fixed to the bone to prevent bone fragments from moving relative to each other. When fixing a bone plate to bone particular care has to be taken in case of peri-implant fractures, including periprosthetic fractures, for example. Periprosthetic fractures are fractures around a joint prosthesis, whereas peri-implant fractures more generally denote fractures around an implant.

When a periprosthetic fracture is to be treated, wherein a prosthetic device (e.g., with a ball joint and a stem) partially extends into a medullary canal of the fractured bone, the surgeon generally has to keep in mind that the fixation elements must not intrude into the medullary canal where the prosthetic device has been inserted. In such cases, an attachment device can be used which is adapted to accommodate the bone plate.

U.S. Pat. No. 4,973,332 and U.S. Pat. Pub. No. 2010/0262194 each discloses periprosthetic repair systems comprising a femur plate and an attachment device. The femur plates shown are configured to hold fracture parts of the femur together to promote healing of the fractured bone, for example. The attachment devices are adapted to be arranged on the femur plates. Specifically, the attachment devices form a partial overlay which fits over and accommodates the femur plate.

The attachment devices known from U.S. Pat. No. 4,973,332 and U.S. Pat. Pub. No. 2010/0262194 include finger-like structures or wings that are inclined with respect to a central portion of the attachment devices and are adapted to extend around at least a portion of the femur. For anchoring the attachment devices in the femur, each wing has a hole for receiving a screw which is screwed into the femur.

When attaching the femur plate using the attachment device, it is desired that this attachment offers a high stability so that the bone fragments of the fractured femur can effectively consolidate. However, when a prosthetic device extends along the length of the femur, the screws for anchoring the attachment device are preferably anchored in the outer hard layer of the bone. That is, they preferably should not penetrate into the medullary canal of the femur.

SUMMARY OF THE INVENTION

It is therefore an object to provide an attachment device which firmly attaches a bone plate to bone and at the same time reduces the risk of fixation elements penetrating the medullary canal.

According to one aspect, an attachment device is provided comprising a central portion having a recess to accommodate the bone plate and at least two lateral wings projecting from the central portion, wherein the lateral wings are arranged on opposite sides of the central portion, wherein each of the two lateral wings comprises a first hole extending through the lateral wing and adapted to accommodate a fixation element therethrough for anchoring the attachment device in bone, wherein the angles of hole axes of the first holes are different with respect to a perpendicular bisector of the centers of the first holes and wherein the hole axes lie outside of the medullary canal.

In order to lie outside the medullary canal, the hole axes may have an angular relationship relative to the perpendicular bisector, to a vertical axis of the central portion (that may be defined within a plane substantially including the hole axes) or to both. In certain implementations, the perpendicular bisector may substantially coincide with the vertical axis of the central portion. The angular relationship may be defined such that the angle between each hole axis and the perpendicular bisector and/or vertical axis of the central portion is less than 45 degrees. In certain implementations (e.g., depending on the anatomical situation), this angle may be less than 35 degrees, less than 25 degrees, less than 20 degrees or less than 15 degrees.

In one aspect, one of the lateral wings is adapted or intended to be arranged on a posterior side and the other lateral wing on an anterior side of the bone. When the attachment device is to be anchored, for example, in a femur or similar bone having an asymmetrical cross-section, there is typically less bone available on the anterior side than on the posterior side. Therefore, the angle between the hole axis and the perpendicular bisector on the anterior side can be smaller than the angle between the hole axis and the perpendicular bisector on the posterior side (e.g., so that the fixation element accommodated in the hole on the posterior side can access the posterior ridge which provides good fixation).

The attachment device may comprise two or more sets of holes. Each set may comprise one hole per lateral wing, and the two holes of each set fulfill the above condition that the angle between the hole axis and the perpendicular bisector on the anterior side is smaller than the angle between the hole axis and the perpendicular bisector on the posterior side. The two or more hole sets may be configured such that each wing comprises a hole intended for the anterior side and another hole intended for the posterior side.

In one realization, the angles of the hole axes with respect to a perpendicular bisector differ by approximately 0.5 to 10 degrees (e.g., between 1 and 6 degrees or 2 to 5 degrees).

The size and shape of the first hole can be different according to the respective requirements. For example, the shape of the hole can be circular or oblong.

In a further implementation, each hole comprises a threaded surface which is adapted to engage with a respective fixation element. The fixation element may have a complementary threaded surface (e.g., in a head region of the fixation element). Each hole may additionally, or alternatively, be adapted to frictionally engage with the fixation element.

In an optional realization, each lateral wing comprises a fixation element supporting area which is adapted to support the fixation element inserted into the first hole, wherein the fixation element supporting area is located opposite to a bone contacting surface of the lateral wing and is arranged at the circumference of the first hole. The fixation element supporting area can be an even (or planar) area which can be arranged concentrically to the hole to which the fixation element supporting area belongs.

The attachment device may essentially be symmetrical. As an example, the attachment device may substantially be symmetrical relative to a longitudinal axis of the central portion. The first holes can be arranged essentially (e.g., within up to 10 mm) equidistant to the longitudinal axis of the central portion.

In one realization, at least one of the lateral wings has at least a second hole, wherein the hole axes of the first and second holes can be different in orientation. The second hole can be arranged adjacent to the first hole, wherein both holes can be arranged essentially (e.g., within up to 10 mm) equidistant to the longitudinal axis of the central portion, or the second hole can be arranged further away from the longitudinal axis than the first hole or vise versa.

In one aspect, the second hole intersects or overlaps the first hole of the lateral wing. As such, a single oblong opening defining both holes may be realized in the lateral wing. The oblong opening may have narrower portion in a central part thereof that delimits the two holes.

In a further aspect, a system comprising the attachment device and fixation elements to anchor the attachment device in bone is provided. The fixation elements may be screws, such as bi-cortical screws. In general, bi-cortical screws enter through the outer hard layer of the bone (corticalis) while the (cancellous) center of the bone is not penetrated. Bi-cortical screws typically offer improved rotational stability compared to other types of fixation elements, like cables or mono-cortical screws. The fixation element can also be a non-compression screw (e.g., a blocking screw) which provides less tension between the screw and the lateral wing than a compression screw.

According to a second aspect of the present invention there is an attachment device for fixing a bone plate to a bone having a medullary canal. The attachment device comprises a central body portion forming a recess to accommodate at least a portion of the bone plate, and two lateral fixation support members arranged on opposite sides of the central body portion, the two lateral fixation support members each having a first hole with a central longitudinal axis, at least a portion of the first holes adapted to accommodate a fixation element therethrough for anchoring the attachment device to the bone. A first bisector line of the central body portion passes through both central longitudinal axes of the first holes. One of the first holes is angled with respect to the perpendicular bisector at a first angle and the other of the first holes is angled with respect to the perpendicular bisector at a second angle with the first and second angles being different.

In one embodiment of this second aspect, the two lateral fixation support members each include a second hole with a central longitudinal axis, at least a portion of the second holes adapted to accommodate a fixation element therethrough for anchoring the attachment device to the bone. At least a portion of the first and second holes of each of the two lateral fixation support members overlap each other.

In another embodiment of this second aspect, one of the second holes is angled with respect to the perpendicular bisector at a third angle and the other of the first holes is angled with respect to the perpendicular bisector at a fourth angle, wherein the third angle is different than the first and fourth angles.

In yet another embodiment of this second aspect, the central body portion includes an upper surface flanked by side surfaces extending downwardly from a portion of the upper surface, the upper surface and side surfaces forming the recess to accommodate at least a portion of the bone plate.

In still yet another embodiment of this second aspect, the attachment device further comprises first and second elongated apertures on the upper surface of the central body portion thereof, the first and second elongated apertures extending from an outer surface of the upper surface of the central body portion through to a bone plate contacting surface and are adapted to receive a fixation member for attaching the attachment device to the bone plate. A second bisector line connecting central points of the first and second elongated apertures is perpendicular to the first bisector line connecting midpoints of the first holes of the two lateral fixation support members. A central point is located on the central body portion, wherein the first and second bisector lines intersect at the central point.

In still yet another embodiment of this second aspect, a first portion of the two lateral fixation support members are part of the side surfaces of the central body portion and a second portion of the two lateral fixation support members project outwardly and inferiorly from the side surfaces of the central body portion.

In still yet another embodiment of this second aspect, when the bone plate is located in the recess of the central body portion, the central axes of the first holes do not intersect a longitudinal axis of the medullary canal.

In still yet another embodiment of this second aspect, the first and second holes of the two lateral fixation support members extend from an outer surface of a respective one of the lateral fixation support members through to a bone contacting surface.

A method for attaching a bone plate to a bone having a medullary canal is also provided, wherein the method comprises the steps of implanting a first fixation element into the bone through the hole of one of the lateral wings, and implanting a second fixation element into the bone through the hole of the other lateral wing, wherein the first fixation element and the second fixation element lie outside of the medullary canal.

Another method for attaching a bone plate to a bone having a medullary canal is also provided. The method includes using an attachment device having a central portion with a recess to accommodate the bone plate and at least two lateral fixation support members projecting from the central portion, wherein the lateral fixation support members are arranged on opposite sides of the central portion. Each lateral fixation support member comprises a first hole extending through the lateral fixation support member and are adapted to accommodate a fixation element therethrough to fix the attachment device to the bone, wherein the angles of hole axes of the first holes are different with respect to a perpendicular bisector of the centers of the first holes. The method comprises the steps of implanting a first fixation element into the bone through the first hole of one of the lateral fixation support members and implanting a second fixation element into the bone through the first hole of the other lateral fixation support member, wherein the first fixation element and the second fixation element lie outside of the medullary canal.

BRIEF DESCRIPTION OF THE DRAWINGS

The foregoing objects, features, aspects and advantages will become more apparent from the following detailed description when taken in conjunction with the accompanying drawings, in which:

FIG. 3 is a sectional view showing the attachment device with respect to line A-A of FIG. 2;

FIG. 4 is a sectional view showing the attachment device with respect to line B-B of FIG. 2;

DETAILED DESCRIPTION

Figure 1:
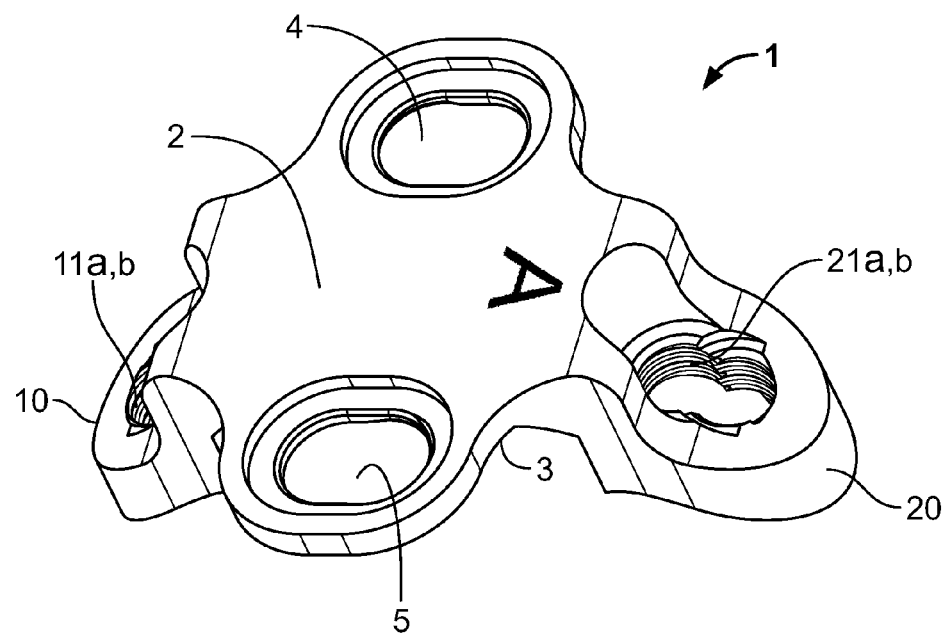
FIG. 1 is a perspective view showing an embodiment of an attachment device.

Hereinafter, embodiments of the attachment device will be described with reference to the accompanying drawings. The same reference numerals are used to refer to identical or similar elements.

Figure 2:
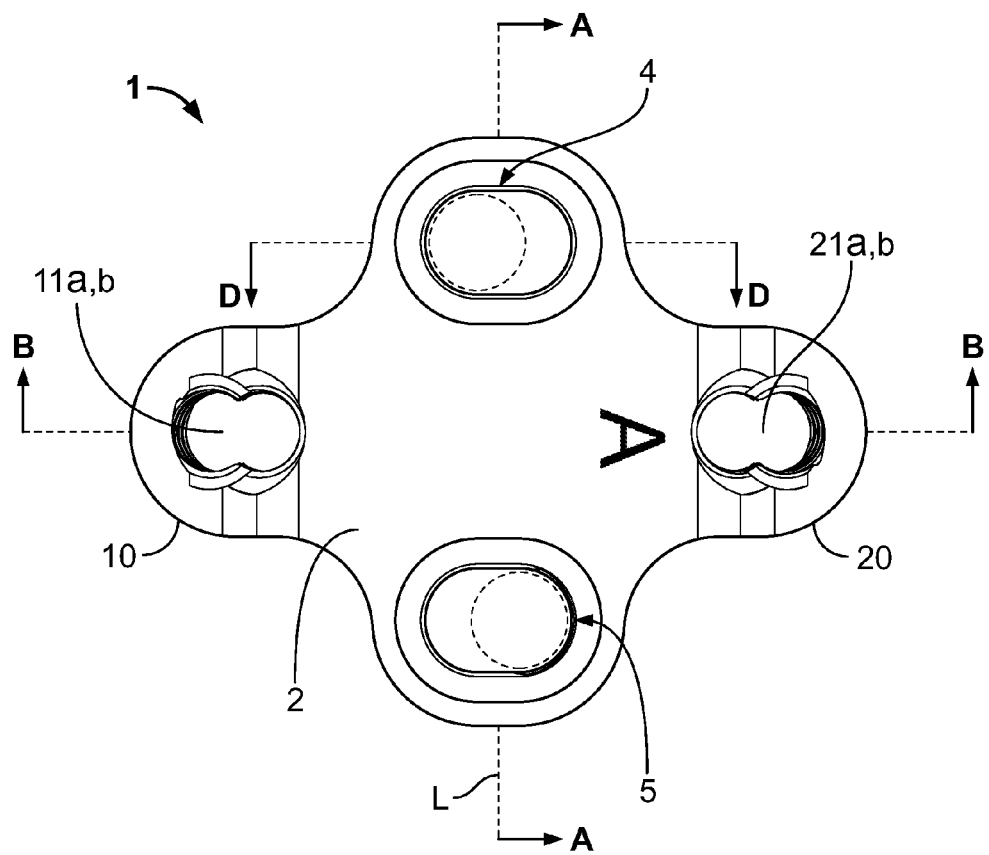
FIG. 2 is a top view showing the attachment device of FIG. 1.

FIGS. 1, 2 and 3 show different views of a first embodiment of the attachment device 1. The attachment device 1 has a cross-like shape and comprises a central portion 2 which has an upper surface directed away from the bone to be treated (not shown) and a lower surface located opposite to the upper surface and directed towards the bone. The central portion 2 on its lower surface defines a recess 3. This recess 3 is sized and shaped to accommodate a bone plate (not shown) to be attached to bone. The attachment device 1 can be placed in any position along a shaft of the bone plate.

Further, the attachment device 1 comprises two lateral wings 10, 20 which are arranged on opposite sides of the central portion 2 and are sized and shaped to conform to the bone to be treated. With additional reference to FIGS. 4 and 5a, the lateral wings 10, 20 extend laterally away from sidewalls of the central portion 2. The wings 10, 20 are inclined or curved to conform (e.g., wrap around) a bone 8 in which the attachment device 1 is to be anchored. The wings 10, may optionally be made of a material that allows a bending of the wings 10, 20 to facilitate conforming of the wings 10, to the bone 8 by a surgeon.

Each lateral wing 10, 20 comprises two holes 11a, 11b, 21a, 21b which are adapted to each accommodate a fixation element to anchor the attachment device 1 in the bone 8. The holes 11a, 11b, 21a, 21b of each wing 10, 20 may in principle be arranged adjacent (e.g., in a row), parallel to a longitudinal axis L of the central portion 2 or, as in the present embodiment, perpendicular with respect to the longitudinal axis L. In the hole arrangement of the present embodiment, both holes 11a, 11b, 21a, 21b of each wing 10, 20 are arranged in an overlapping configuration and define a single oblong opening.

It will be understood that multiple configurations with respect to the number of holes and number of lateral wings are possible. The number of holes and/or lateral wings on the two sides of the central portion 2 can also be different. It will be understood that the attachment device 1 may in certain embodiments comprise more than two (e.g., four) wings.

The central portion 2 has a top part arranged along the longitudinal axis L of the central portion 2 and two sidewalls which extend perpendicularly to the top part and are arranged on opposite sides thereof, resulting in a U-like shape of the central portion 2. The thickness of the top part of the central region 2 may be in a range of 0.5 to 4 mm (e.g., 1.5 mm). The width of the top part of the central portion 2 may be in a range of 8 to 17 mm. The sidewalls of the central portion 2 have the same size and shape and may have a height in a range of 3 to 15 mm.

The recess 3 is formed by the two sidewalls and the top part of the central portion 2. The sidewalls need not tightly fit against the corresponding sides of a bone plate accommodated in the recess 3 since the top part may be connected to the bone plate. To this end, the central portion 2 comprises two or more holes 4, 5 which extend through the top part and which are adapted to each accommodate a fixation element which is inserted into a plate hole of a bone plate accommodated in the recess 3. Each hole 4, 5 of the central portion 2 has an oblong shape perpendicular to the longitudinal axis L and a threaded surface to engage with a respective fixation element (having a mating threaded surface). The diameter of each central portion hole 4, 5 may be in a range of 3 to 8 mm (e.g., 5 mm). The distance between the centers of the holes 4, 5 may be in a range of 10 to 25 mm (e.g., 18 mm).

Figure 5A:
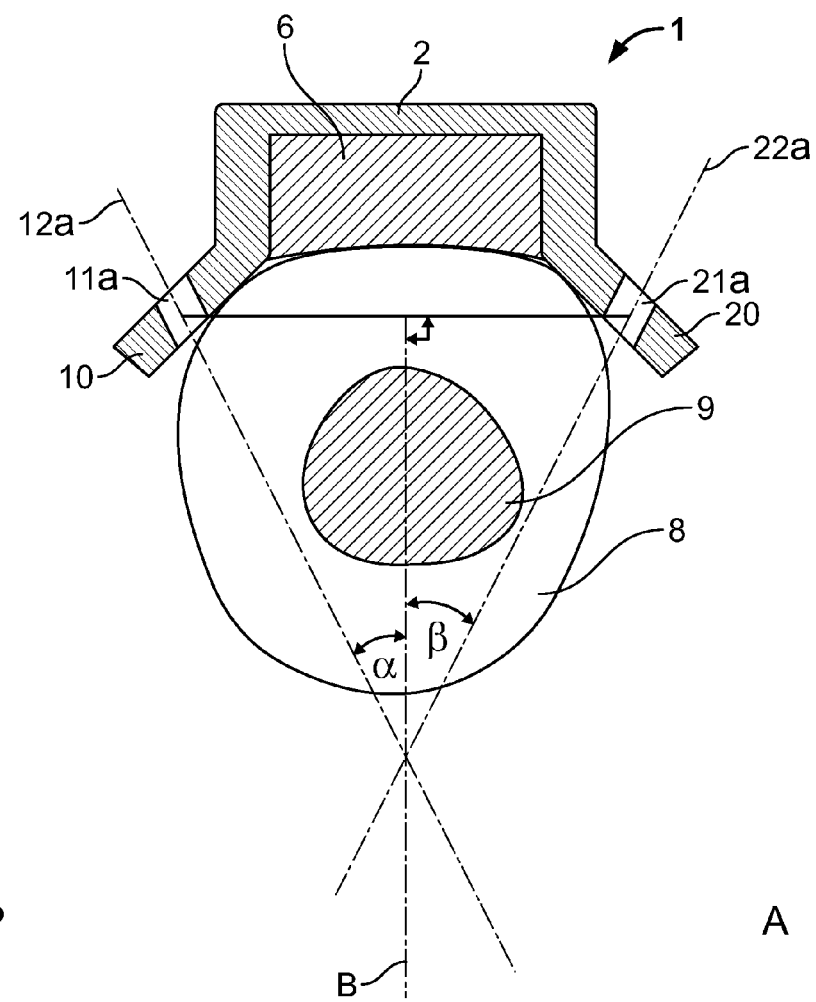
FIG. 5a is a sectional view schematically showing a bone plate attached to an asymmetrical bone by the attachment device.
Figure 5B:
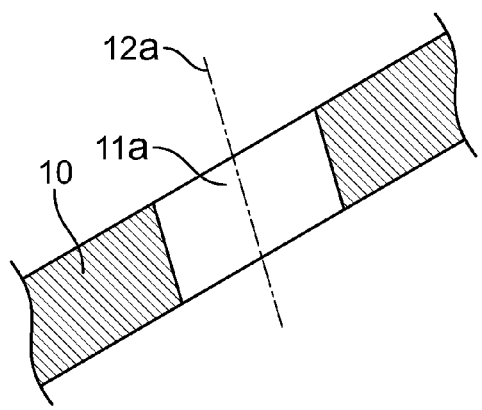
FIG. 5b is a sectional view based on FIG. 5a showing the center of the hole at the hole axes.

As shown in FIGS. 4, 5a and 5b, the holes 11a, 11b, 21a, 21b of the lateral wings 10, 20 have hole axes which each defines an angle with respect to a perpendicular bisector B of the centers of two corresponding holes 11a, 11b, 21a, 21b of opposite wings 10, 20. A perpendicular bisector is a line which is positioned perpendicularly to a line connecting two such hole centers. The perpendicular bisector has the property that each of its points is equidistant from the centers of the holes. For certain hole configurations, the perpendicular bisector may coincide with a vertical axis of the central portion 2 that perpendicularly extends through the longitudinal axis L.

A center of a hole may be defined as a point which is arranged on the hole axis in the middle between a bone contacting surface of the lateral wing and a surface of the lateral wing which is arranged opposite to the bone contacting surface, as shown in FIG. 5b. Thus, each hole axis intersects or crosses the perpendicular bisector B defining an angle therebetween ($\alpha$, $\beta$), as shown in FIG. 5a. The distance between the two hole centers of each wing 10, 20 is less than the sum of the radii of the two holes 12a, 12b, 22a, 22b, giving rise to an overlap.

The two overlapping holes 11a, 11b, 21a, 21b per wing 10, 20 have hole axes 12a, 12b, 22a, 22b which are inclined relative to each other. The hole axes 12a, 12b, 22a, 22b of the holes 11a, 11b, 12a, 12b of the lateral wings 10, are arranged in one plane which is perpendicular to the longitudinal axis L of the central portion 2. Moreover, the attachment device 1 is symmetrical to this plane, as shown in FIG. 2.

The hole configuration of each wing 10, 20 comprises an inside hole 11a, 21a arranged next to the longitudinal axis L of the central portion 2 and an outside hole 11b, 21b being further away from the longitudinal axis L than the inside hole 11a, 21a. The distance between the centers of the holes 11a, 11b, 12a, 12b and the perpendicular bisector B, for example for the holes 11a, 21a, may be in a range of 8 to 16 mm. As an example, the distance between the center of the hole 11a to the perpendicular bisector B may be mm and between the center of the hole 11b to the perpendicular bisector B may be 14 mm. Further, the distance between the center of the hole 21a to the perpendicular bisector B may be 12 mm and between the center of the hole 21a to the perpendicular bisector B may be 14 mm.

As illustrated in the schematic drawing of FIG. 5a, the attachment device 1 is adapted to accommodate a bone plate 6 in its recess 3, wherein a bone contacting surface of the lateral wings 10, 20 generally follows the contour of the bone 8. The angles of the hole axes 12a, 22a of two holes 11a, 21a of opposite wings 10, 20 are different with respect to the perpendicular bisector B of the centers of the holes 12a, 21a such that the hole axes 12a, 22a lie outside of a medullary canal 9 of the bone 8 (e.g., a femur). In order to lie outside the medullary canal, the hole axes 12a, 22a have a defined angular relationship relative to the perpendicular bisector B (or to the vertical axis of the central portion 2).

Specifically, the hole axes 12a, 22a of the holes 11a, 21a are arranged such that they intersect an outer hard layer of the bone 8, but lie outside the medullary canal 9. Thus, a fixation element, for example a bi-cortical screw, can be inserted into the outer hard layer of the bone 8 through the hole 11a, 21a without passing the medullary canal 9, but still providing a good anchoring. FIG. 5a illustrates that a thicker outer hard layer of the bone is available on the posterior side P than on the anterior side A. Thus, an angle β between the hole axis 22a and the perpendicular bisector B on the center of the holes 11a, 21a is defined to be smaller than the angle α between the hole axis 12a and the perpendicular bisector B so that an optimal anchoring of the attachment device 1 is provided.

As illustrated in FIG. 4 in greater detail, in the present embodiment the angle between the hole axis 12a of the inside hole 11a and the perpendicular bisector B is 7.8 degrees (with a tolerance of 1 degree) and the angle between the hole axis 22a of the inside hole 21a and the perpendicular bisector B is 5.8 degrees (with a tolerance of 1 degree). Further, the angle between the hole axis 12b of the outside hole 11b and the perpendicular bisector B is 11.4 degrees (with a tolerance of 1 degree). The angle between the hole axis 22b of the outside hole 21b and the perpendicular bisector B is 9.4 degrees (with a tolerance of 1 degree).

In the embodiments illustrated in FIGS. 4 and 5a, the lateral wing 10 is arranged on a posterior side P and the other lateral wing 20 is arranged on an anterior side A of the bone 8. The angle β of the hole axis 12a, 22a on the anterior side A is smaller with respect to the perpendicular bisector than the angle α of the hole axis 12a, 22a of the lateral wing on the posterior side P. Such an angular relationship provides for a maximum anchoring since the larger bone thickness of the posterior ridge on the posterior side P can efficiently be exploited as illustrated in FIG. 5a.

Since the hole axes have different angles with respect to the perpendicular bisector B as illustrated in FIGS. 4 and 5a, the sides of the attachment device 1 may be marked so that the surgeon can easily identify the different hole arrangements. Therefore, one lateral wing 20 of the attachment device 1 arranged on the anterior side A is thus marked with a capital letter "A", as shown in FIGS. 1 and 2, wherein the other lateral wing 10 arranged on the posterior side P is not specifically identified.

Figure 6:
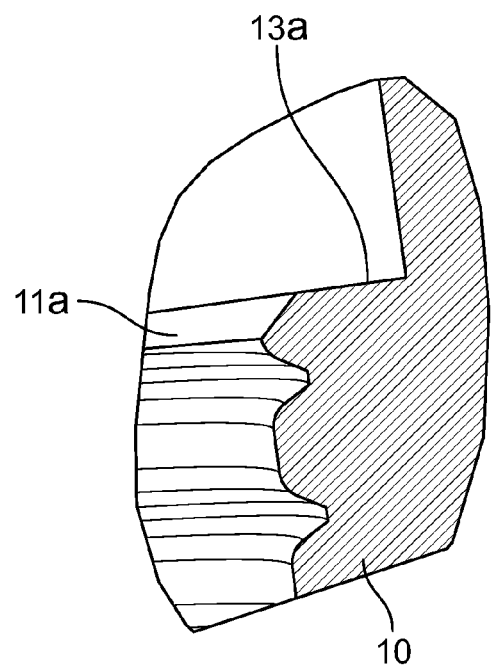
FIG. 6 is a partial perspective view showing a fixation element supporting area surrounding a hole of the attachment device.

FIG. 6 shows a partial sectional view of the lateral wing 10 together with hole 11a. Therein, a planar fixation element supporting area 13a is shown which is adapted to support the fixation element, for example, a bi-cortical screw, inserted into hole 11a. The fixation element supporting area 13a is located opposite to the bone contacting surface of the lateral wing 10 and is arranged at the circumference of hole 10a. Moreover, the fixation element supporting area 13a is even, or flat, to provide a contact surface (for example for a non-compression or any other screw). Specifically, the fixation element supporting area 13a defines a first level and the upper surface of the lateral wing 10 defines a second level, wherein the first level is below the second level.

In should be noted that the lateral wing 10 of FIG. 6 has not to be compressed to the bone to achieve fixation. In one realization, the lateral wing 10 is anchored to the bone 8 by means of a long bi-cortical screw inserted into the outer hard layer of the bone 8, rather than by applying compression to the lateral wing 10 by means of a compression screw. A fixation element supporting area 13a as illustrated in FIG. 6 can also be provided for the other holes of the lateral wings 10, 20.

FIG. 6 further shows that hole 11a comprises a threaded surface which is adapted to engage with a respective fixation element, in particular a bi-cortical screw, which has a complementary threaded surface. Moreover, all holes of the lateral wings 10, 20 may comprise such a threaded surface.

Figure 7:
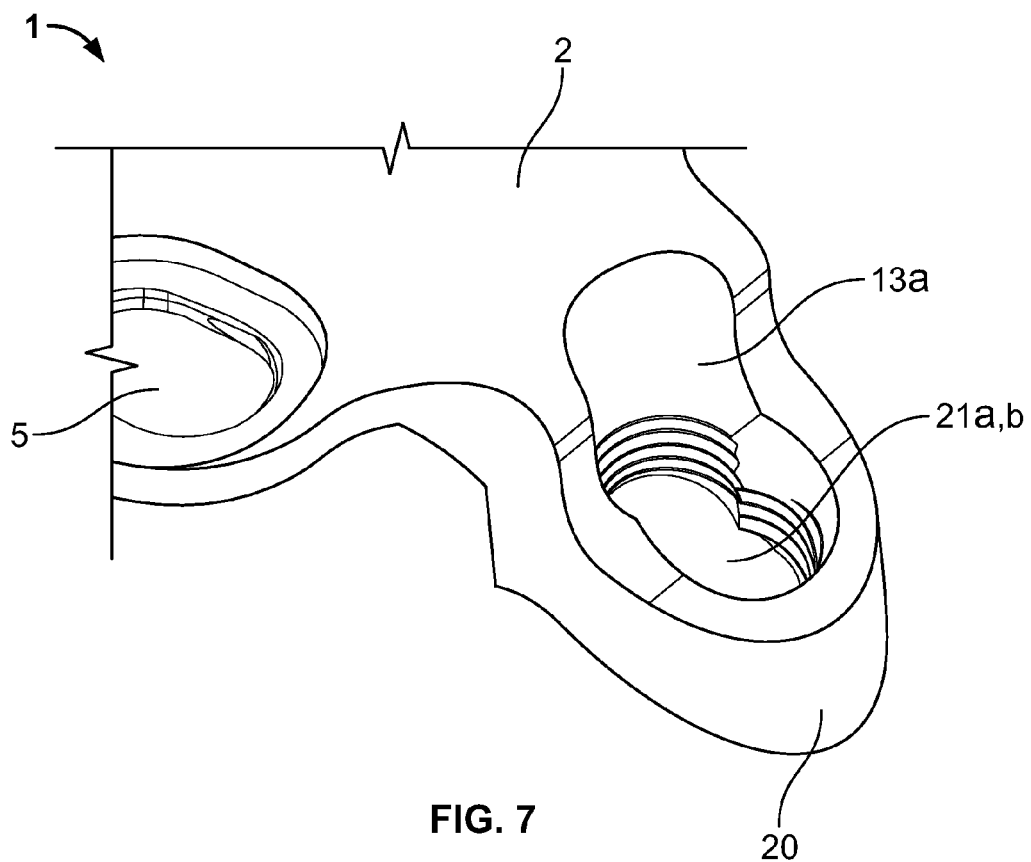
FIG. 7 is a partial perspective view showing a lateral wing the attachment device.

FIG. 7 shows a partial perspective view of the attachment device 1 in a further realization and highlights the lateral wing 20 with overlapping holes 21a, 21b and a part of the central portion 2 with a central portion hole 5. As illustrated in FIG. 7, the fixation element supporting area 13a could alternatively be defined to comprise curved (e.g., substantially spherical) surface portions.

Figure 8:
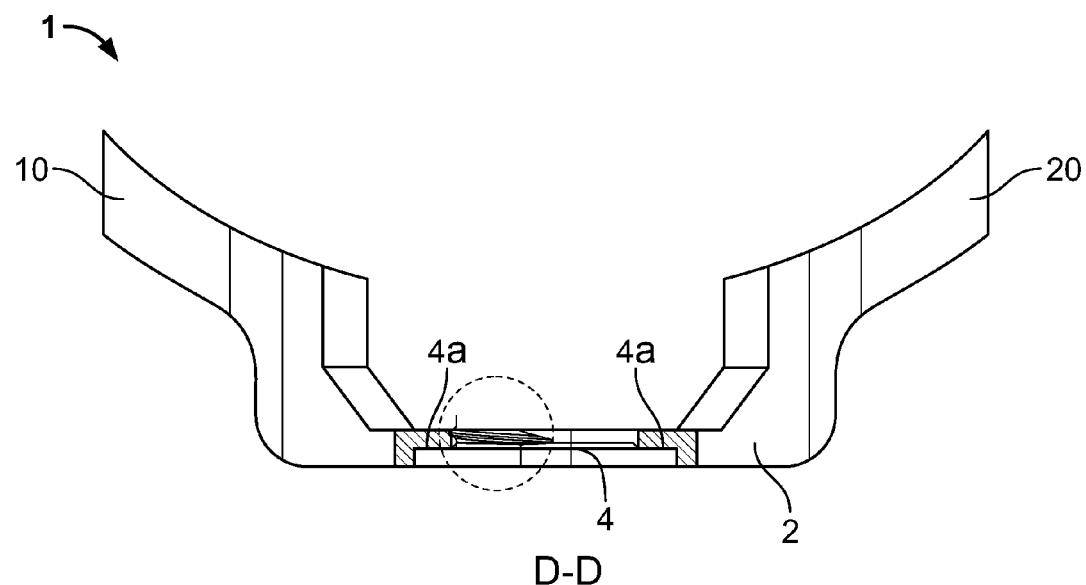
FIG. 8 is a sectional view showing the attachment device with respect to line D-D of FIG. 2.

FIG. 8 is a sectional view of the attachment device showing the central portion hole 4 together with an even supporting area 4a. Further, it is shown that the central portion hole 4 has a threaded surface just like the holes of the lateral wings 10, 20.

Figure 9:
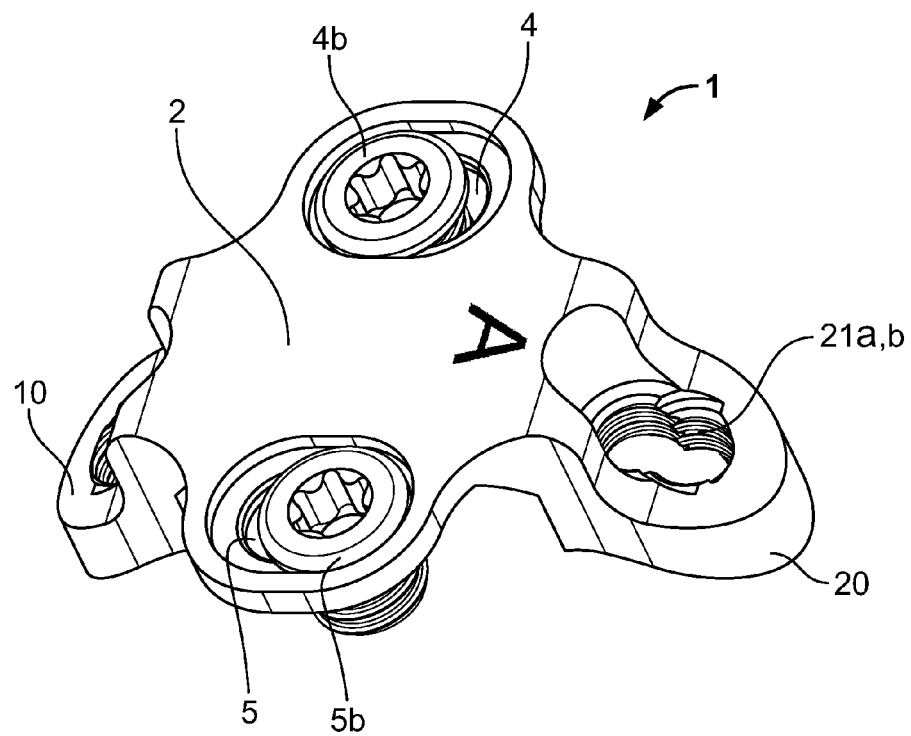
FIG. 9 is a perspective view showing the attachment device with two fixation elements inserted into the central portion holes.
Figure 10:
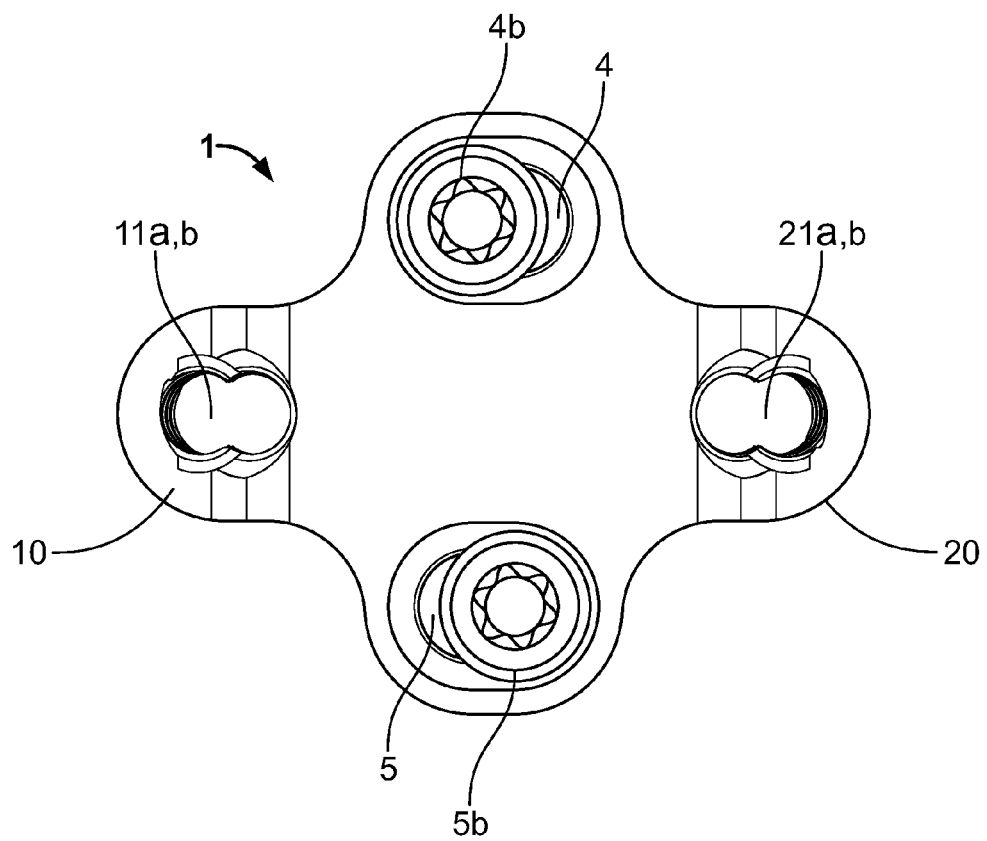
FIG. 10 is a top view showing the attachment device of FIG. 9.
Figure 11:
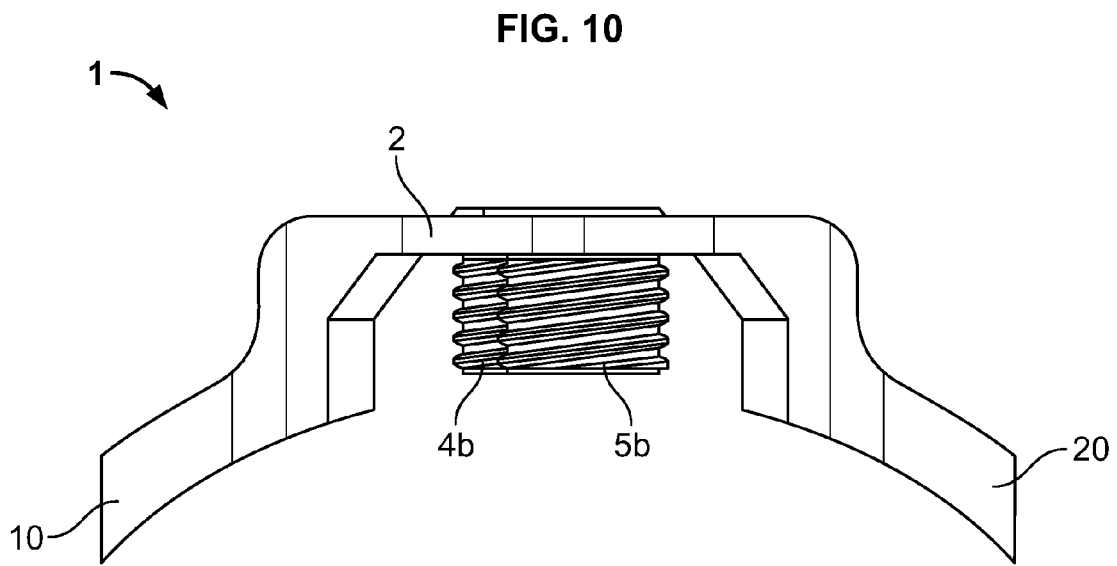
FIG. 11 is a side view showing the attachment device of FIG. 9.

With additional reference to FIGS. 9 to 11, the holes 4, 5 of the central portion 2 are sunken so as to receive the fixation elements 4a, 5a (in the form of screws) such that the fixation elements 4a, 5a protrude minimally, or do not protrude at all, over the upper surface of the attachment device 1 as defined by the top part of the central portion 2. The length of the holes 4, 5 in the elongated direction is larger than a shaft diameter of the fixation elements 4a, 5a to be inserted into the central portion holes 4, 5 to attach the attachment device 1 to the bone plate 6. Such a dimensioning will allow guided movement of the attachment device 1 with respect to the bone plate when the fixation elements 4a, 5a are loosely inserted therein. In other words, due to the elongate shape of the holes 4, 5, the loosely inserted screws 4b, 5b increase the ability to easily slide the attachment device 1 over the bone plate 6 within a range defined by the elongate holes 4, 5 to find the best position to fix the attachment device 1 to the bone plate 6 and/or the bone 8.

Figure 12:
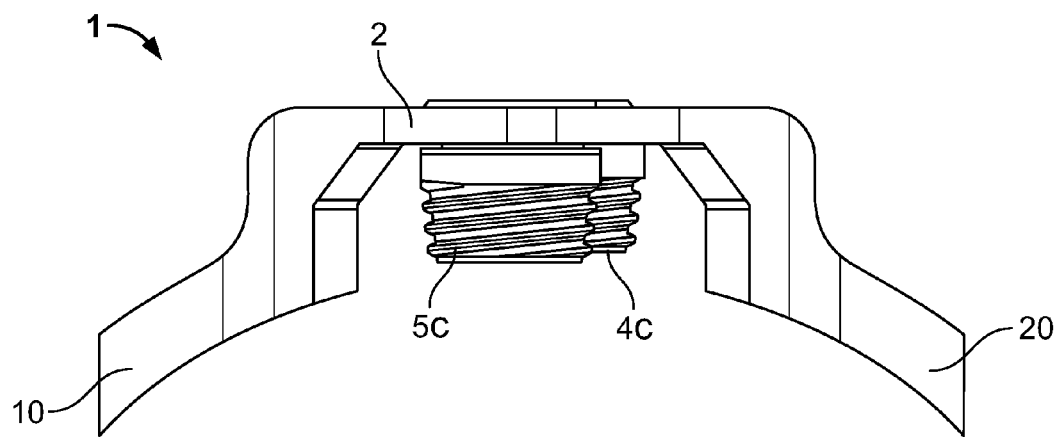
FIG. 12 is a side view showing the attachment device with conical inserts inserted into the central portion holes.
Figure 13:
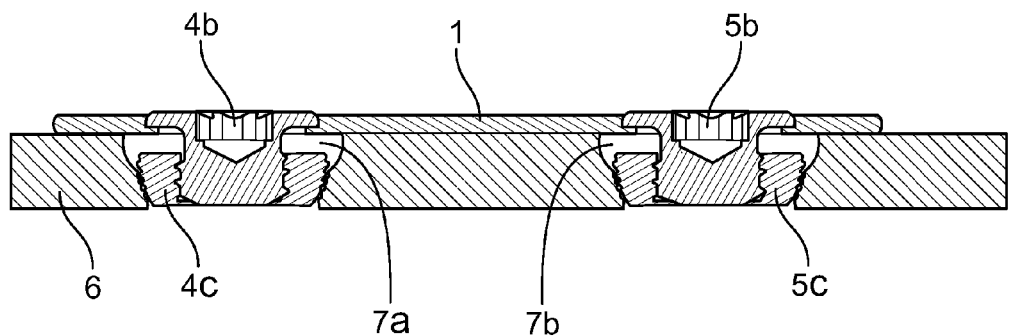
FIG. 13 is a sectional view showing a connection between the attachment device and the bone plate by means of fixation elements together with conical inserts.

FIGS. 12 and 13 show views of the attachment device 1 in a further realization. Here, conical locking inserts 4c, 5c are provided that accommodate fixation elements in the form of screws 4b, 5b and each comprise a threaded internal surface which corresponds to the threaded surface of the screws 4b, 5b. Further, the conical inserts 4c, 5c have for locking purposes an external thread which corresponds to a threaded surface of a bone plate hole 7a, 7b of the bone plate 6.

When the attachment device 1 is to be connected to the bone plate 6, the conical inserts 4c, 5c are inserted into the bone plate holes 7a, 7b. Thereby, the conical inserts 4c, 5c are slightly keyed with their external threaded surfaces to the threaded surfaces of the bone plate hole 7a, 7b. When screwing in the screws 4b, 5b, compression is applied to the attachment device 1 due to the conical inserts 4c, 5c. This compression results in a locking connection between the attachment device 1 and the bone plate 6.

Figure 14:
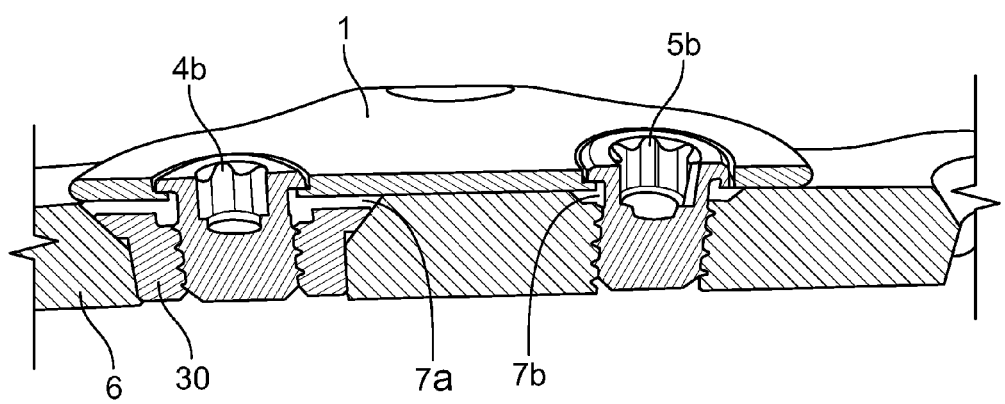
FIG. 14 is a perspective sectional view showing a further connection between the attachment device and the bone plate.

FIG. 14 shows a further connection type between the attachment device 1 and the bone plate 6 having a locking insert 30 which is also inserted into the central portion holes 4, 5 like conical insert 4c, 5c. This locking insert 30 does not have an external thread so that only a frictional engagement between the locking insert 30 and the central portion 4, 5 can be accomplished. The locking insert 30 comprises an internal thread to engage with the screws 4b, 5b. Further, FIG. 14 shows a regular screw connection between the attachment device 1 and the bone plate 6 by means of a screw 5b with a threaded surface and a corresponding threaded surface at the central portion hole 7b of the bone plate 6.

Hereinafter, a periprosthetic procedure for attaching the attachment plate 1 presented herein to bone will be described with exemplary reference to FIG. 5a.

First, the surgeon attaches the attachment device 1 to the bone plate 6 by means of screws 4b, 5b, wherein the bone plate 6 is already (at least provisionally) fixed to the bone 8 along the longitudinal axis of the bone 8. Further, since the hole axes 12a, 22a of the holes 11a, 21a arranged at the lateral wings 10, 20 are intersecting the outer hard layer of the bone, whereby the hole axes 12a, 22a lie outside of the medullar channel 9, the surgeon first implants a bi-cortical screw through one of the holes 11a, 21a into the outer hard layer of the bone and fixes therewith the lateral wing 10, 20 to the bone. Hereby it is possible that there is still a certain spacing between the lateral wing 10, 20 and the bone surface since a compression is typically not necessary here (the bi-cortical screw provides a better anchoring than, for example, a mono-cortical conical screw).

Thereafter, the surgeon implants a further bi-cortical screw through the hole 11a, 21a of the other lateral wing 10, 20, whereby the bi-cortical screw again does not pass the medullary canal 9. Thus, both lateral wings 10, 20 of the attachment device 1 are securely anchored to the bone 8 at different angles α, β.

As has become apparent from the above, the angle between a hole axis of a lateral wing and the perpendicular bisector may be adapted to an anatomy of a bone so that the hole axis of the respective hole is directed to this part of the bone where there is enough outer hard layer of the bone to provide a good anchoring. For an asymmetrical bone, the angles will be different for lateral wings on opposite sides.

Having described preferred embodiments of the invention referring to the accompanying drawings, it should be understood that the present disclosure is not limited to those embodiments. Various chances and modifications thereof may be made by one skilled in the art without departing from the scope of the claims appended hereto.

The invention claimed is:

1. An orthopedic system comprising:
 a bone plate having a bone contacting surface and an opposing surface and a plurality of apertures extending through the bone contacting and opposing surfaces; and
 an attachment plate comprising:
  an elongated central body portion contacting the opposing surface of the bone plate, the elongated central body portion extends along a central longitudinal axis between opposing ends defining a vertical length of the attachment plate, the elongated central body portion forming an elongated recess to accommodate therein at least a portion of the bone plate, the elongated central body portion having first and second elongated apertures extending therethrough, the central longitudinal axis passing through a center of each of the first and the second elongated apertures located adjacent the opposing ends of the elongated central body portion, the first and the second elongated apertures configured to align with at least one of the plurality of apertures of the bone plate to receive a fixation member for attaching the attachment plate to the bone plate; and
  a first lateral fixation support member extending at a fixed angle from a first side surface of the elongated central body portion and a second lateral fixation support member extending at a fixed angle from a second side surface of the elongated central body portion opposite to the first side surface, the first and the second lateral fixation support members each having a respective end defining a horizontal width of the attachment plate, the first and the second lateral fixation support members each having first and second overlapping holes extending therethrough along first and second hole axes lying along a central plane about the horizontal width, the central plane being perpendicular to the central longitudinal axis of the central body portion and passing through a center of the attachment plate, the first and the second overlapping holes of each of the first and the second lateral fixation support members adapted to accommodate a fixation element therethrough for anchoring the attachment device to the bone,
 wherein a first bisector line of the elongated central body portion lies within the central plane and passes through both hole axes of the first and the second overlapping holes of each of the first and the second lateral fixation support members,
 wherein the central longitudinal axis and the first bisector line perpendicular thereto intersect at the center of the attachment plate, the first and the second elongated apertures each being offset from the center of the attachment plate, and
 wherein the hole axis of one of the first holes is angled with respect to the first bisector line at a first angle and the hole axis of the other of the first holes is angled with respect to the first bisector line at a second angle, the first angle being different than the second angle, and
 wherein the hole axis of one of the second holes is angled with respect to the first bisector line at a third angle and the hole axis of the other of the second holes is angled with respect to the first bisector line at a fourth angle, wherein the first, second, third and fourth angles are different than one another.

2. The orthopedic system of claim 1, wherein the first and second holes of each of the first and second lateral fixation support members extend from an outer surface of a respective one of the first and second lateral fixation support members to a bone contacting surface of the respective one of the first and second lateral fixation support members.

3. The orthopedic system of claim 1, wherein the elongated central body portion includes an upper surface flanked by the first and second side surfaces extending downwardly from a portion of the upper surface, the upper surface and side surfaces forming the recess to accommodate at least a portion of the bone plate.

4. The orthopedic system of claim 1, wherein each of the first and second lateral fixation support members project outwardly and inferiorly from the first and second side surfaces of the central body portion.

5. The orthopedic system of claim 1, wherein the angles of the hole axes of the first and second holes differ by approximately 0.1 to 10 degrees.

6. The orthopedic system of claim 1, wherein each of the first and second holes comprises a threaded surface which is adapted to engage with the respective fixation element.

7. The orthopedic system of claim 1, wherein each of the first and second lateral fixation support members comprises a fixation element supporting area which is adapted to support the respective fixation element inserted into the first hole thereof, wherein the fixation element supporting area is located opposite to a bone contacting surface of each of the first and second lateral fixation support members and is arranged about a circumference of the first holes, wherein the fixation element supporting area is configured to be even.

8. The orthopedic system of claim 7, wherein the fixation element supporting area is configured to support the respective fixation element on a first level and a surface of each of the first and second lateral fixation support members surrounding the fixation element supporting area is configured to define a second level above the first level.

9. The orthopedic system of claim 7, wherein the respective fixation elements are bi-cortical screws.

10. An orthopedic system comprising:
 a bone plate having a bone contacting surface and an opposing surface and a plurality of apertures extending through the bone contacting and opposing surfaces; and
 an attachment plate comprising:
  an elongated central body portion contacting the opposing surface of the bone plate, the elongated central body portion extends along a central longitudinal axis between opposing ends defining a vertical length of the attachment plate, the elongated central body portion forming an elongated recess to accommodate therein at least a portion of the bone plate, the elongated central body portion having first and second elongated apertures extending therethrough, the central longitudinal axis passing through a center of each of the first and the second elongated apertures located adjacent the opposing ends of the elongated central body portion, the first and the second elongated apertures configured to align with at least one of the plurality of apertures of the bone plate to receive a fixation member for attaching the attachment plate to the bone plate; and
 a first lateral fixation support member extending at a fixed angle from a first side surface of the elongated central body portion and a second lateral fixation support member extending at a fixed angle from a second side surface of the central body portion opposite to the first side surface, the first and the second lateral fixation support members each having a respective end defining a horizontal width of the attachment plate, the first and the second lateral fixation support members each having two overlapping holes extending therethrough, each with a hole axis lying along a central plane about the horizontal width, the central plane being perpendicular to the central longitudinal axis of the elongated central body portion and passing through a center of the attachment plate, the two overlapping holes of each of the first and the second lateral fixation support members adapted to accommodate a fixation element therethrough for anchoring the attachment device to the bone,
wherein a first bisector line of the central body portion lies within the central plane and passes through each hole axis of the two overlapping holes of the first and second lateral fixation support members,
wherein the hole axis of one of the two overlapping holes of the first lateral fixation support member is angled with respect to the first bisector line at a first angle, the hole axis of one of the two overlapping holes of the second lateral fixation support member is angled with respect to the first bisector line at a second angle, the hole axis of the other of the two overlapping holes of the first lateral fixation support member is angled with respect to the first bisector line at a third angle, and the hole axis of the other of the two overlapping holes of the second lateral fixation support member is angled with respect to the first bisector line at a fourth angle, the first, second, third and fourth angles being different than one another,
wherein the central longitudinal axis of the elongated central body portion and the first bisector line perpendicular thereto intersect at the center of the attachment plate, and
wherein the first and the second elongated apertures are offset from the center of the attachment plate.

* * * * *